(12) United States Patent
Vidal et al.

(10) Patent No.: US 10,308,895 B2
(45) Date of Patent: Jun. 4, 2019

(54) SYNERGISTIC PERFUMING COMPOSITION

(71) Applicant: Firmenich SA, Geneva (CH)

(72) Inventors: Jorge Pablo Vidal, Buenos Aires (AR); Messias Antonio Ferraz Shimizu, Sao Paulo (BR); Axel Voelker, Sao Paulo (BR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/553,085

(22) PCT Filed: Feb. 24, 2016

(86) PCT No.: PCT/EP2016/053861
§ 371 (c)(1),
(2) Date: Aug. 23, 2017

(87) PCT Pub. No.: WO2016/135193
PCT Pub. Date: Sep. 1, 2016

(65) Prior Publication Data
US 2018/0245018 A1    Aug. 30, 2018

(30) Foreign Application Priority Data
Feb. 25, 2015   (EP) .................................... 15156481

(51) Int. Cl.
*C11B 9/00* (2006.01)
*A61Q 13/00* (2006.01)
*A61K 8/44* (2006.01)

(52) U.S. Cl.
CPC ............ *C11B 9/0003* (2013.01); *A61K 8/447* (2013.01); *A61Q 13/00* (2013.01); *C11B 9/00* (2013.01); *C11B 9/003* (2013.01); *C11B 9/0015* (2013.01); *C11B 9/0019* (2013.01)

(58) Field of Classification Search
CPC ..................................................... C11B 9/0003
See application file for complete search history.

(56) References Cited

U.S. PATENT DOCUMENTS

2014/0323383 A1* 10/2014 Trujillo .............. C11D 17/0039
510/439

FOREIGN PATENT DOCUMENTS

| WO | WO2003049666 A2 | 6/2003 |
| WO | WO2012113746 A1 | 8/2012 |
| WO | WO2014176392 A1 | 10/2014 |

OTHER PUBLICATIONS

International Preliminary Report on Patentability (Chapter I), Appl. No. PCT/EP2016/053861, dated Aug. 29, 2017.
International Search Report and Written Opinion, application PCT/EP2016/053861 dated May 19, 2016.

* cited by examiner

*Primary Examiner* — Arrie L Reuther
(74) *Attorney, Agent, or Firm* — Winston & Strawn LLP

(57) ABSTRACT

The present invention relates to the field of perfumery and more precisely it concerns a perfuming composition, and the consumer articles associated therewith, showing an improved impact of fragrance intensity and/or modulating fragrance character. The perfuming composition of matter comprises a β-thio carbonyl profragrance derivative and specific perfuming terpenes derivatives.

19 Claims, No Drawings

SYNERGISTIC PERFUMING COMPOSITION

RELATED APPLICATIONS

This application is a national stage application under 35 U.S.C. § 371 filing of International Patent Application PCT/EP2016/053861, filed Feb. 24, 2016, which claims the benefit of European patent application n° 15156481.2 filed Feb. 25, 2015.

TECHNICAL FIELD

The present invention relates to the field of perfumery and more precisely it concerns a perfuming composition, and the consumer articles associated therewith, showing an improved impact of fragrance intensity and/or modulating fragrance character. The perfuming composition comprises a β-thio carbonyl profragrance derivative and specific perfuming terpenes derivatives.

BACKGROUND

As mentioned above the present invention is aimed at impacting the overall fragrance intensity and in particular the top notes and/or the bottom notes (top and bottom notes are well known terms in the art), in particular those associate with specific perfuming ingredients.

The so called "top notes" of a perfume are the perfuming ingredients which are perceived immediately upon, and overall the first hours after, application of a perfume and form a consumer's initial impression of a perfume and thus are very important in the performance and the selling of the product. Therefore it is quite interesting to have compositions which allows to improve the impact of the top notes.

The so called "bottom notes" of a perfume are the perfuming ingredients which are perceived long after application of a perfume and form a consumer's long lasting impression of a perfume and thus are also very important in the performance and the selling of the product. Therefore it is quite interesting to have compositions which allow improving the impact of the bottom notes.

The β-thio carbonyl profragrance derivative of formula (I) herein below described have been described in WO 03/049666, however they are known by a person skilled in the art, and as exemplified in the cited document, as having a release profile being significant after several hours. So it was totally unexpected to found that the compound himself, in addition to the slow release of a perfume, do have also an immediate effect on the perception of some top notes.

DESCRIPTION OF THE INVENTION

The present invention relates to a perfuming composition of matter, which is capable of synergistically improving the intensity and the impact of the fragrance intensity, in particular top notes, in the first hours of utilization. Said a perfuming composition of matter is particularly adapted for fine fragrance and/or bodycare/cosmetic uses.

Consequently, a first object of the present invention is a perfuming composition comprising, or even consisting of:
a) at least one β-thio carbonyl profragrance derivative of formula

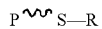  S—R     (I)

wherein the wavy line indicates the location of the bond between said P and the sulfur atom;

P represents a group of the formulae (P-1) to (P-9), in the form of any one of their isomers:

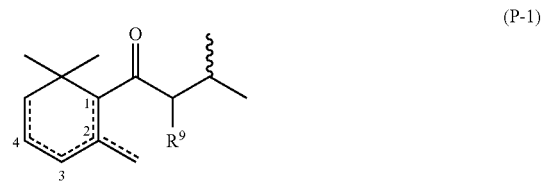 (P-1)

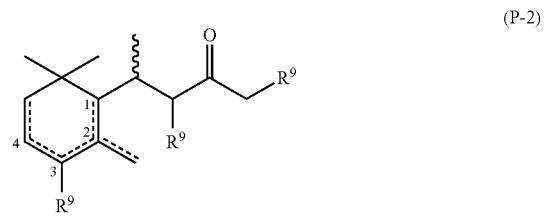 (P-2)

 (P-3)

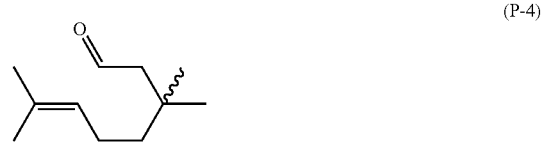 (P-4)

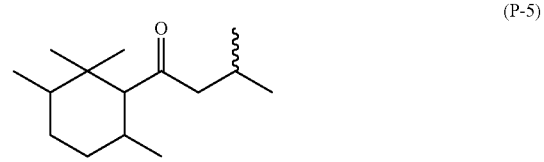 (P-5)

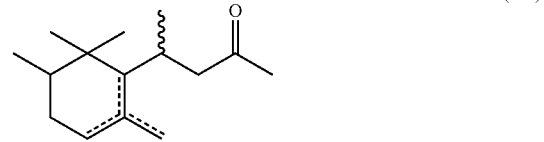 (P-6)

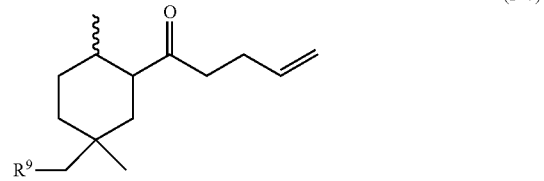 (P-7)

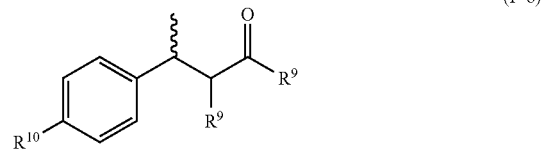 (P-8)

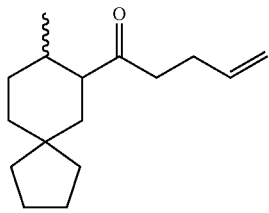
(P-9)

in which formulae the wavy lines have the meaning indicated above and the dotted lines represent a single or double bond, and $R^9$ being a hydrogen atom or a methyl group; and R represents a linear or branched alkyl group having from 8 to 15 carbon atoms, optionally comprising a carboxylic functional group which is not directly linked to the sulphur atom; and b) at least one perfume ingredient selected among:
acyclic mono-terpenes derivatives; and/or
musk compounds;
said components a) and b) being present in a w/w (weight to weigh) ratio a)/b) comprised between 1/1 and 1/4500.

According to any embodiment of the invention, a particularly appreciated embodiment is effect observed on top notes, therefore component b) may be selected amongst acyclic mono-terpenes derivatives, and musk compounds are optional ingredients.

According to any embodiment of the invention, w/w (weight to weigh) ratio a)/b) can be comprised between 1/1 and 1/450, or even between 1/2 and 1/100, or between 1/3 and 1/80, or between 1/3 and 1/25.

According to any embodiment of the invention, said β-thio carbonyl profragrance derivative of formula (I) is a derivative wherein P is a group of the formulae (P-1), (P-2), (P-5) or (P-6), as defined above. In particular said P can be a group of the formulae (P-1) or (P-2), wherein $R^9$ represent a hydrogen atom.

According to any embodiment of the invention, said R represents a linear alkyl group having from 8 to 15 carbon atoms, optionally comprising a carboxylic functional group which is not directly linked to the sulphur atom. In particular said R can be a linear alkyl group having from 10 to 14 carbon atoms, and in particular a n-dodecyl group.

According to any embodiment of the invention, and as non-limiting examples of such β-thio carbonyl profragrance derivative of formula (I) one may cites the following: 3-(dodecylthio)-1-(2,6,6-trimethylcyclohex-3-en-1-yl)butan-1-one (derived from δ-damascone, also known and referred as Haloscent® D) or 3-(dodecylthio)-1-(2,6,6-trimethylcyclohex-2-en-1-yl)butan-1-one (derived from α-damascone) or 4-(dodecylthio)-4-(2,6,6-trimethylcyclohex-2-en-1-yl)butan-2-one (derived from ionone, also known and referred as Haloscent® I), a mixture thereof.

For the sake of clarity, by the wording "acyclic perfuming mono-terpenes derivatives", or the similar, it is meant here all perfuming ingredients which are acyclic and are alcohols, aldehydes, ketones, esters, ethers, or nitriles of mono-terpene compounds and which are useful in perfuming preparations or compositions to impart a hedonic effect. In other words such an "acyclic perfuming mono-terpenes derivatives", to be considered as such, must be recognized by a person skilled in the art as being able to impart or modify in a positive or pleasant way the odor of a composition, and not just as having an odor. A person skilled in the art of perfumery knows very well which compound is comprised in such definition and by the way many of these acyclic perfuming mono-terpenes derivatives are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery.

According to any embodiment of the invention, said acyclic perfuming mono-terpenes derivatives can be alcohols, aldehydes, acetates or nitriles derivatives and in particular alcohols, aldehydes, acetates.

The "acyclic perfuming mono-terpenes derivatives" herein described are considered by perfumers as belonging to the so called "top notes" which are perceived immediately upon application of a perfume and form a person's initial impression of a perfume and thus are very important in the selling of the product. Therefore it is quite interesting to have a composition which allows improving the impact of the top notes.

According to any embodiment of the invention and as non-limiting examples of such acyclic perfuming mono-terpenes derivatives one may cites the following:
geraniol, nerol, citronellol, dihydrolinalool, linalool ethyl linalool, myrcenol, dihidro myrcenol;
citral, 3-Me-citral, citronellal, geranial, hydroxycitronellal;
citronellyl acetate, linalyl acetate, geranyl acetate, linalyl propionate, neryl acetate, linalyl caproate, geranyl tiglate;
linalyl methyl ether; and/or
citronellyl nitrile;
said compounds being in the form of anyone of its stereoisomers or of any mixture thereof; and the underlined compound being particularly appreciated ones.

Some of these acyclic perfuming mono-terpenes derivatives are natural compound and can be also incorporated in the form of natural essential oils, but of course accounted only for their amount of such compounds for the purpose of calculating the ration a)/b).

For the sake of clarity, by the wording "musk compound", or the similar, it is meant here all perfuming ingredients which are recognized by a person skilled in the art as being perfuming ingredient of the musk family. The musk family is a very well established family of odorant and is widely described in the literature. In other words such an "musk compound", to be considered as such, must be recognized by a person skilled in the art as being able to impart or modify in a positive or pleasant way the odor of a composition, and not just as having an odor of the musk type. A person skilled in the art of perfumery knows very well which compound is comprised in such definition and by the way many of these acyclic perfuming mono-terpenes derivatives are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery.

According to any embodiment of the invention, said musk compound can be a ketone, and acetal, or an ester or lactone derivatives.

The "musk compound" herein described are considered by perfumers as belonging to the so called "bottom notes" which are perceived long after application of a perfume and form a person's long lasting impression of a perfume and thus are very important in the selling of the product. Therefore it is quite interesting to have a composition which allows modifying/modulating the impact of the bottom notes.

According to any embodiment of the invention and as non-limiting examples of such musk compounds one may cites the following:

(1S,1'R)-2-[1-(3',3'-dimethyl-1'-cyclohexyl)ethoxycarbonyl]methyl propanoate (also known as Romandolide®), (1S,1'R)-2-[1-(3',3'-dimethyl-1'-cyclohexyl)ethoxy]-2-methylpropyl propanoate (also known as Helvetolide®), 2-[1-(3,3-dimethylcyclohexyl)ethoxy]-2-methylpropyl cyclopropanecarboxylate (also known as Serenolide®), 2-[(3,5-dimethyl-3-hexen-2-yl)oxy]-2-methylpropyl cyclopropanecarboxylate (also known as Serenolide®), 1-[(1R)-3,3-dimethylcyclohexyl]ethyl ethyl propanedioate (also known as Applelide); and/or 1-oxa-12-cyclohexadecen-2-one (also known as Habanolide®), oxacyclohexadecan-2-one (also known as Exaltolide®), 1,4-dioxacycloheptadecane-5,17-dione (also known as Astrotone), 3-methyl-(4/5)-cyclopentadecenone (also known as Muscenone®), muscone, (Z)-4-cyclopentadecen-1-one (also known as Exaltenone®), 9-cycloheptadecen-1-one and/or 1,3,4,6,7,8-hexahydro-4,6,6,7,8,8-hexamethyl-cyclopenta-[G] isochromene (also known as Galaxolide®)

said compounds being in the form of anyone of its stereoisomers or of any mixture thereof; and the underlined compound being particularly appreciated ones.

According to any embodiment of the invention, the perfuming composition of matter may further comprise, as optional components, some other perfuming ingredients which have been surprisingly found to contribute also to the perceived synergies. Said optional components, can be selected amongst:

methyl 2-(3-oxo-2-pentylcyclopentyl)acetate (e.g. also known as Hedione®), (+)-methyl (1R)-cis-3-oxo-2-pentyl-1-cyclopentaneacetate (e.g. also known as Paradisone®), benzyl salicylate, tetrahydro-2-isobutyl-4-methyl-4(2H)-pyranol, 3-benzodioxole-5-propionaldehyde (Heliopropanal); and/or coumarine, and/or 1-(octahydro-2,3,8,8-tetrame-2-naphthalenyl)-1-ethanone (also known as Iso E® Super);

said compounds being in the form of anyone of its stereoisomers or of any mixture thereof; and the underlined compound being particularly appreciated ones.

Said optional components can be present in a w/w (weight to weigh) ratio optional components)/b) comprised between 0 and 4/1, or even comprised between 1/10 and 2/1.

As mentioned above, the perfuming composition of matter above described show an increased the overall fragrance intensity, and in particular the top note, which are perceived over the first hours of application. Therefore another object of the present invention is the use as perfuming ingredients of the invention's perfuming composition of matter. In particular, and in other words, a method to boost, enhance, modulating, improve or increase the odor properties (in particular the intensities and the time profile) of a perfuming composition or of a perfumed consumer product, which method comprises adding to said composition or consumer product an effective amount of the perfuming composition of matter according to the invention. For instance, the overall effect imparted by the use of said composition of matter is thus a blooming effect.

By "use of the perfuming composition of matter" it has to be understood here also the use of any composition containing said composition of matter and which can be advantageously employed in perfumery industry as active ingredients.

Therefore, another object of the present invention is a perfuming composition comprising:

i) as perfuming ingredient, an invention's perfuming composition of matter as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as butylene or propylene glycols, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Generally speaking, by "perfumery base" we mean here a composition comprising at least one perfuming co-ingredient.

Moreover, by "perfuming co-ingredient" it is meant here a compound, which is used in a perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulfurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the sake of clarity, said perfuming co-ingredients are different from the acyclic perfuming mono-terpenes derivatives as cited above, as well as from the β-thio carbonyl profragrance derivative of formula (I) as cited above.

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), color agents (e.g. dyes and/or pigments), preservative (e.g. antibacterial or antimicrobial or antifungi or anti irritant agents), abrasives, skin cooling agents, fixatives, insect repellants, ointments, vitamins and mixture thereof.

Other suitable perfumery adjuvant optionally used can be tertiary amines, in particular those with high water solubility, such as triethanolamine, methyldiethylamine, methyldiethanolamine, dimethylethanolamine, alkyldiethanolamines and ethoxylated alkyldiethanolamines.

Furthermore, an invention's perfuming composition of matter, or a perfuming composition comprising it, can be advantageously used in all the fields of modern perfumery, such as fine perfumery or functional perfumery, in particular in those applications requiring a blooming effect, or an increased impact/perception within hours. Therefore, the invention's perfuming composition of matter may be incorporated in any application requiring, or having a benefit from, a blooming effect as to increase the perception/impact of the top notes (i.e. the odor impact in the first hours). In general, such application are in particular aimed for an application on the skin or hair, and according to anyone of the invention's embodiments, said perfuming consumer product is a perfuming consumer product having a total amount of surfactant below 20%, 15%, 10% w/w, or even below 6% or 1% w/w, the percentage being relative to the weight of the perfuming consumer product formulation (i.e. without the packaging).

Consequently, a perfuming consumer product having a total amount of surfactant below 20%, 15%, 10% w/w, or even below 6% or 1% w/w, the percentage being relative to the weight of the perfuming consumer product formulation (i.e. without the packaging), comprising, as a perfuming ingredient, a perfuming composition of matter defined above, is also an object of the present invention.

For the sake of clarity, it has to be mentioned that, by "perfuming consumer product" it is meant a consumer product which is expected to deliver at least a pleasant perfuming effect to the surface to which it is applied (e.g. skin or hair). In other words, a perfuming consumer product according to the invention is a perfumed consumer product which comprises the functional formulation, as well as optionally additional benefit agents, corresponding to the desired consumer product, e.g. an eau de toilette, and an olfactive effective amount of the invention's perfuming composition of matter.

The nature and type of the constituents of the perfuming consumer product do not warrant a more detailed description here, which in any case would not be exhaustive, the skilled person being able to select them on the basis of its general knowledge and according to the nature and the desired effect of said product.

According to anyone of the invention's embodiments, said perfuming consumer product is a perfume (such as a fine perfume, eau de toilette, eau de perfume, cologne, body splash, after shave lotion or body spray, body mist), or a deodorant or antiperspirant (such as a body deodorant spray), or even a cosmetic composition (including but not limiting to a body lotion, cream or gel, shower gels and hair care products).

According to anyone of the invention's embodiments, typically said perfume is a perfuming consumer product having a total amount of surfactant below 6% or 1% w/w, while said deodorant/antiperspirant is a product having a total amount of surfactant below 10% w/w, and the cosmetic composition is a product having a total amount of surfactant below 20% w/w.

Some of the above-mentioned perfuming consumer products may represent an aggressive medium for the components of the invention's perfuming composition of matter, so that it may be necessary to protect the perfuming composition of matter from premature decomposition, for example by encapsulation.

The proportions in which the perfuming composition of matter according to the invention can be incorporated into the various aforementioned products or compositions vary within a wide range of values. These values are dependent on the nature of the product to be perfumed and on the desired olfactory effect as well as the nature of the co-ingredients in a given composition when the composition of matter according to the invention are mixed with perfuming co-ingredients, solvents or additives commonly used in the art.

For example, typical concentrations are in the order of 1% to 30% by weight, or even more, of the invention's compound based on the weight of the composition into which they are incorporated. Concentrations lower than these, such as in the order of 0.1% to 20% by weight, can be used when this compound is applied directly in the perfuming of the various perfuming consumer products mentioned hereinabove.

The invention will now be described in further detail by way of the following examples.

EXAMPLE 1

Preparation of a Perfuming Composition of Matter According to the Invention
1) Binary Compositions
Various perfuming composition were made by admixing various ingredients as per description herein below:
A) Formula without Component a) (Control):
79.580% Ethanol 96°
19.420% Demineralized water
1.000% Perfumery Raw Material
wherein the perfumery raw material is each time an acyclic perfuming mono-terpenes derivative: Linalyl Acetate (A.1), Citral (A.2), Citronellol (A.3), Hydroxycitronellal (A.5), Geranyl Acetate (A.6), Linalol (A.8), Citronellyl Acetate (A.9), Citronellal (A.11), Citronellyl Nitrile (A.12), Methylcitral (A.13), Dihydrolinalol (A.14), or a musk: Romandolide® (A.15), Helvetolide® (A.16), Exaltolide® (A.17), Astrotone® (A.18), Habanolide® (A.19).
B) Formula with Component a) (Haloscent® D): ratio a)/b)=1/4.44
79.580% Ethanol 96°
18.970% Demineralized water
0.225% Component a)
0.225% Triethanol amine
1.000% Perfumery Raw Material * wherein the perfumery raw material is each time either
- an acyclic perfuming mono-terpenes derivative: Linalyl Acetate (A.1.i), Citral (A.2.i), Citronellol (A.3.i), Hydroxycitronellal (A.5.i), Geranyl Acetate (A.6.i), Linalol (A.8.i), Citronellyl Acetate (A.9.i), Citronellal (A.11.i), Citronellyl Nitrle (A.12.i), Methylcitral (A.13.i), Dihydrolinalol (A.14.i) or
- a musk: Romandolide® (A.15.i), Helvetolide® (A.16.i), Exaltolide® (A.17.i)

C) Formula with Delta Damascone:
79.580% Ethanol 96°
18.970% Demineralized water
0.225% Delta Damascone
0.225% Triethanol amine
1,000% Perfumery Raw Material *
wherein the perfumery raw material is each time an acyclic perfuming mono-terpenes derivative: Linalyl Acetate (A.1.c), Citral (A.2.c), Citronellol (A.3.c)

D) Formula with Component a) (Haloscent® I): ratio a)/b)=1/4.44
79.580% Ethanol 96°
18.970% Demineralized water
0.225% Component a)
0.225% Triethanol amine
1.000% Perfumery Raw Material *
wherein the perfumery raw material is each time either:
- an acyclic perfuming mono-terpenes derivative: Citral (D.1.i), Citronellal (D.2.i), Citronellyl Nitrle (D.3.i), Methylcitral (D.4.i), Dihydrolinalol (D.5.i), or
- a musk: Romandolide® (D.6.i), Helvetolide® (D.7.i), Exaltolide® (D.8.i), Astrotone® (D.9.i), Habanolide® (D.10.i)

2) Ternary Compositions

Various perfuming composition were made by admixing various ingredients as per description herein below:

E) Formula without Haloscent® D or Haloscent® (Control—Binary Combination)
79.580% Ethanol 96°
18.420% Demineralized water
1.000% Perfumery Raw Material *
1.000% Perfumery Raw Material *
wherein each time one perfumery raw material is an acyclic perfuming mono-terpenes derivative and the other perfumery raw material is either a musk, or another acyclic mono-terpene, or an optional ingredient: Romandolide®+Citronellol (E.1), Romandolide®+Linalyl Acetate (E.2), Paradisone®+Linalyl acetate (E.3), Helvetolide®+Linalyl Acetate (E.6), Helvetolide®+Citronellol (E.7), Exaltolide®+Linalyl Acetate (E.8), Geraniol+Linalyl Acetate (E.9), Hedione®+Linalyl Acetate (E.10), Hedione®+Citronellol (E.11), Salicylate de Benzyle+Linalyl Acetate (E.12)

F) Formula with Component a) (Haloscent® D):
Ratio a)/b)=1/4.44
Ratio b)/ratio optional components)=1/1
79.580% Ethanol 96°
17.970% Demineralized water
0.225% Component a)
0.225% Triethanol amine
1.000% Perfumery Raw Material *
1.000% Perfumery Raw Material *
wherein each time one perfumery raw material is an acyclic perfuming mono-terpenes derivative and the other perfumery raw material is either a musk, or another acyclic mono-terpene, or an optional ingredient: Romandolide®+Citronellol (E.1.i), Romandolide®+Linalyl Acetate (E.2.i), Paradisone®+Linalyl acetate (E.3.i), Helvetolide®+Linalyl Acetate (E.6.i), Helvetolide®+Citronellol (E.7.i), Exaltolide®+Linalyl Acetate (E.8.i), Geraniol+Linalyl Acetate (E.9.i), Hedione®+Linalyl Acetate (E.10.i), Hedione®+Citronellol (E.11.i), Benzyl salicylate+Linalyl Acetate (E.12.i)

G) Formula without Component Haloscent® I (Control)
79.580% Ethanol 96°
19.320% Demineralized water
0.100% Perfumery Raw Material*
1.000% Perfumery Raw Material*
Wherein each time one perfumery raw material is respectively an acyclic perfuming mono-terpenes derivative (0.1%) and the other perfumery raw material is a musk (1%): Citronellol+Romandolide® (G.1), Methylcitral+Helvetolide® (G.2).

H) Formula with Component a) Haloscent® I
Ratio a)/b)=1/4.44
79.580% Ethanol 96°
18.970% Demineralized water
0.225% Haloscent I
0.225% TEA
0.100% Perfumery Raw Material*
1.000% Perfumery Raw Material*
Wherein each time one perfumery raw material is respectively an acyclic perfuming mono-terpenes derivative (0.1%) and the other perfumery raw material is a musk (1%): Citronellol+Romandolilde® (G.1.i), Methylcitral+Helvetolide® (G.2.i).

I) Formula without Components a) Haloscent D and Haloscent® I (Control)
79.580% Ethanol 96°
19.420% Demineralized water
1.000% Perfumery Raw Material *
Wherein each time the perfumery raw material is either an acyclic perfuming mono-terpenes derivative, or a musk: Citral (I.1), Citronellol (I.2), Astrotone (I.3), Exaltolide® (I.4), Romandolide® (I.5), Helvetolide® (I.6)

J) Formula with to Components a) Haloscent® D and Haloscent® I
Ratio a)/b)=1/2.22
79.580% Ethanol 96°
18.520% Demineralized water
0.225% Haloscent® D
0.225% Haloscent® I
0.450% TEA
1,000% Perfumery Raw Material *
Wherein each time the perfumery raw material is either an acyclic perfuming mono-terpenes derivative, or a musk: Citral (I.1.i), Citronellol (I.2.i), Astrotone (I.3.i), Exaltolide® (I.4.i), Romandolide® (I.5.i), Helvetolide® (I.6.i)

Olfactive Evaluation of the Invention's Composition of Matter:

The tests were carried out using a standard protocol to obtain directional guidance on the strength of the odor. An aliquot (40 μl) of composition was deposited on a glass surface at 32° C., and after different time intervals, according to the examples below, 8 to 10 panelists (trained to evaluate fragrance intensity) were asked to blindly evaluate fragrance intensity of the samples on a 7 point categorical scale (1=No odour to 7=Extremely strong odour).

The results then analyzed according to a balanced design (Latin square). The data of the 8 to 10 panelists are averaged and conclusions are drawn based on difference in scores by pairs of products and the level of agreement between the panelists.

There were three possible outputs:

1—No Difference between the two products: The difference in average scores between the two products was lower than 0.5 and/or the assessors were not in agreement in their evaluation;

2—Directional tendency for a difference between the two products: There was a difference in average scores between the two products of at least 0.5 and there was a good agreement between the assessors (i.e.: between 60 to 70% of panelists agreeing that one sample is more intense than another and no more than 15% of panelists saying the inverse)

3—Strong tendency for a difference between the two products: There was a difference in average scores between the two products of at least 0.5 and there was a strong agreement between the assessors (i.e.: 70% of panelists or more agreeing that one sample is more intense than another)

The following average odor intensities at different evaluation times are reported in the following Tables:

TABLE 1

Linalyl Acetate vs (Linalyl Acetate + Haloscent ® D*)

| Evaluation point | A.1 | A.1.i | Result |
|---|---|---|---|
| 15 minutes | 1.7 | 2.9 | A.1 << A.1.i |

*= 3-(dodecylthio)-1-(2,6,6-trimethylcyclohex-3-en-1-yl)butan-1-one; origin: Firmenich SA

TABLE 2

(Linalyl Acetate) vs (Linalyl Acetate + Delta Damascone)

| Evaluation point | (A.1) | (A.1.c) | Result |
|---|---|---|---|
| 15 minutes | 1.7 | 1.9 | (A.1) = (A.1.c) |

TABLE 3

(Citral) vs (Citral + Haloscent ® D)

| Evaluation point | A.2 | A.2.i | Result |
|---|---|---|---|
| 15 minutes | 4.7 | 5.8 | A.2 << A.2.i |
| 30 minutes | 3.6 | 3.9 | A.2 = A.2.i |

TABLE 4

(Citronellol) vs (Citronellol + Haloscent ® D)

| Evaluation point | A.3 | A.3.i | Result |
|---|---|---|---|
| 15 minutes | 4.2 | 5.0 | A.3 << A.3.i |
| 30 minutes | 4.4 | 5.0 | A.3 < A.3.i |
| 45 minutes | 3.2 | 3.7 | A.3 = A.3.i |

TABLE 5

(Hydroxycitronellal) vs (Hydroxycitronellal + Haloscent ® D)

| Evaluation point | A.5 | A.5.i | Result |
|---|---|---|---|
| 15 minutes | 3.1 | 3.8 | A.5 = A.5.i |
| 2 hours | 1.5 | 2.2 | A.5 << A.5.i |
| 3 hours | 2.1 | 1.9 | A.5 = A.5.i |

TABLE 6

(Geranyl Acetate) vs (Geranyl Acetate + Haloscent ® D)

| Evaluation point | A.6 | A.6.i | Result |
|---|---|---|---|
| 15 minutes | 4.3 | 4.3 | A.6 = A.6.i |
| 2 hours | 3.2 | 3.3 | A.6 = A.6.i |
| 3 hours | 1.9 | 2.7 | A.6 << A.6.i |

TABLE 7

(Linalol) vs (Linalol + Haloscent ® D)

| Evaluation point | A.8 | A.8.i | Result |
|---|---|---|---|
| 15 minutes | 3.0 | 4.4 | A.8 << A.8.i |

TABLE 8

(Citronellyl Nitrile) vs. (Citronellyl Nitrile + Haloscent ® D)

| Evaluation point | A.9 | A.9.i | Result |
|---|---|---|---|
| 15 minutes | 4.6 | 4.4 | A.9 = A.9.i |
| 2 hours | 1.5 | 2.7 | A.9 << 9.i |
| 3 hours | 1.5 | 2.7 | A.9 << A.9.i |

TABLE 9

(Citronellal) vs (Citronellal + Haloscent ® D)

| Evaluation point | A.11 | A.11.i | Result |
|---|---|---|---|
| 15 minutes | 3.3 | 4.8 | A.11 << A.11.i |
| 2 hours | 1.9 | 2.1 | A.11 = A.11.i |
| 3 hours | 2.0 | 2.1 | A.11 = A.11.i |

TABLE 10

(Citronellyl Nitrile) vs (Citronellyl Nitrile + Haloscent ® D)

| Evaluation point | A.12 | A.12.i | Result |
|---|---|---|---|
| 15 minutes | 2.6 | 2.8 | A.12 = A.12.i |
| 2 hours | 2.4 | 3.0 | A.12 << A.12.i |
| 3 hours | 2.1 | 2.3 | A.12 = A.12.i |

TABLE 11

(Methylcitral) vs (Methylcitral + Haloscent ® D)

| Evaluation point | A.13 | A.13.i | Result |
|---|---|---|---|
| 15 minutes | 2.3 | 3.3 | A.13 << A.13.i |
| 2 hours | 2.2 | 2.6 | A.13 = A.13.i |
| 3 hours | 1.0 | 1.7 | A.13 = A.13.i |

TABLE 12

(Dihydrolinalol) vs (Dihydrolinalol + Haloscent ® D)

| Evaluation point | A.14 | A.14.i | Result |
|---|---|---|---|
| 15 minutes | 2.7 | 3.5 | A.14 < A.14.i |

TABLE 13

(Romandolide ®) vs (Romandolide ® + Haloscent ® D)

| Evaluation point | A.15 | A.15.i | Result |
|---|---|---|---|
| 15 minutes | 2.5 | 2.9 | A.15 = A.15.i |
| 2 hours | 2.7 | 3.8 | A.15 << A.15.i |
| 3 hours | 2.4 | 3.8 | A.15 << A.15.i |

TABLE 14

(Helvetolide ®) vs (Helvetolide ® + Haloscent ® D)

| Evaluation point | A.16 | A.16.i | Result |
|---|---|---|---|
| 15 minutes | 3.4 | 4.0 | A.16 << A.16.i |
| 2 hours | 2.3 | 2.7 | A.16 = A.16.i |
| 3 hours | 2.2 | 3.2 | A.16 << A.16.i |

TABLE 15

(Exaltolide ®) vs (Exaltolide ® + Haloscent ® D

| Evaluation point | A.17 | A.17.i | Result |
|---|---|---|---|
| 15 minutes | 3.0 | 4.1 | A.17 << A.17.i |
| 2 hours | 2.5 | 3.4 | A.17 << A.17.i |
| 3 hours | 2.0 | 2.9 | A.17 << A.17.i |

TABLE 16

(Citral) vs (Citral + Haloscent ® I)

| Evaluation point | A.2 | D.1.i | Result |
|---|---|---|---|
| 15 minutes | 3.7 | 4.5 | A.2 << D.1.i |
| 2 hours | 2.1 | 3.4 | A.2 << D.1.i |
| 3 hours | 1.8 | 2.9 | A.2 << D.1.i |

TABLE 17

(Citronellal) vs. (Citronellal + Haloscent ® I)

| Evaluation point | A.11 | D.2.i | Result |
|---|---|---|---|
| 15 minutes | 3.3 | 4.2 | A.11 << D.2.i |
| 2 hours | 2.6 | 3.1 | A.11 = D.2.i |
| 3 hours | 1.8 | 2.1 | A.11 = D.2.i |

TABLE 18

(Citronellyl Nitrile) vs. (Citronellyl Nitrile + Haloscent ® I)

| Evaluation point | A.12 | D.3.i | Result |
|---|---|---|---|
| 15 minutes | 3.2 | 3.4 | A.12 = D.3.i |
| 2 hours | 1.9 | 3.8 | A.12 << D.3.i |
| 3 hours | 1.3 | 2.4 | A.12 << D.3.i |

TABLE 19

(Methylcitral) vs (Methylcitral + Haloscent ® I)

| Evaluation point | A.13 | D.4.i | Result |
|---|---|---|---|
| 15 minutes | 2.3 | 3.3 | A.13 << D.4.i |
| 2 hours | 2.2 | 2.6 | A.13 = D.4.i |
| 3 hours | 1.0 | 1.7 | A.13 = D.4.i |

TABLE 20

(Dihydrolinalol) vs (Dihydrolinalol + Haloscent ® I)

| Evaluation point | A.14 | D.5.i | Result |
|---|---|---|---|
| 15 minutes | 2.4 | 4.3 | A.14 << D.5.i |
| 2 hours | 1.7 | 1.7 | A.14 = D.5.i |
| 3 hours | 1.6 | 2.1 | A.14 < D.5.i |

TABLE 21

(Romandolide ®) vs (Romandolide ® + Haloscent ® I)

| Evaluation point | A.15 | D.6.i | Result |
|---|---|---|---|
| 15 minutes | 3.1 | 4.5 | A.15 << D.6.i |
| 2 hours | 3.4 | 4.6 | A.15 << D.6.i |
| 3 hours | 3.0 | 4.7 | A.15 << D.6.i |

TABLE 22

(Helvetolide ®) vs. (Helvetolide ® + Haloscent ® I)

| Evaluation point | A.16 | D.7.i | Result |
|---|---|---|---|
| 15 minutes | 3.9 | 3.9 | A.16 = D.7.i |
| 2 hours | 2.6 | 3.9 | A.16 << D.7.i |
| 3 hours | 3.2 | 3.9 | A.16 < D.7.i |

TABLE 23

(Exaltolide ®) vs Exaltolide ® + Haloscent ® I)

| Evaluation point | A.17 | D.8.i | Result |
|---|---|---|---|
| 15 minutes | 3.4 | 4.3 | A.17 << D.8.i |
| 2 hours | 3.4 | 4.5 | A.17 << D.8.i |
| 3 hours | 2.7 | 3.9 | A.17 << D.8.i |

TABLE 24

(Astrotone) vs (Astrotone + Haloscent ® I)

| Evaluation point | A.18 | D.9.i | Result |
|---|---|---|---|
| 15 minutes | 2.7 | 4.1 | A.18 << D.9.i |
| 2 hours | 2.6 | 3.8 | A.18 << D.9.i |
| 3 hours | 3.0 | 4.0 | A.18 << D.9.i |

TABLE 25

| (Habanolide ®) vs (Habanolide ® + Haloscent ® I) | | | |
|---|---|---|---|
| Evaluation point | A.19 | D.10.i | Result |
| 15 minutes | 3.4 | 4.5 | A.19 << D.10.i |
| 2 hours | 3.8 | 3.5 | A.19 = D.10.i |
| 3 hours | 3.2 | 4.0 | A.19 << D.10.i |

TABLE 26

| (Romandolide ® + Citronelol) vs (Romandolide ® + Citronelol + Haloscent ® D) | | | |
|---|---|---|---|
| Evaluation point | E.1 | E.1.i | Result |
| 15 minutes | 5.5 | 5.5 | E.1 = E.1.i |
| 2 hours | 2.3 | 3.3 | E.1 << E.1.i |
| 3 hours | 1.6 | 2.4 | E.1 << E.1.i |

TABLE 27

| (Romandolide ® + linalyl acetate) vs (Romandolide ® + Linalyl Acetate + Haloscent ® D) | | | |
|---|---|---|---|
| Evaluation point | E.2 | E.2.i | Result |
| 15 minutes | 3.1 | 3.9 | E.2 = E.2.i |
| 45 minutes | 1.9 | 3.1 | E.2 << E.2.i |
| 2 hours | 2.1 | 2.4 | E.2 = E.2.i |
| 3 hours | 2.1 | 2.7 | E.2 = E.2.i |

TABLE 28

| (Paradisone ® + Linalyl Acetate) vs (Paradisone ® + Linalyl Acetate + Haloscent ® D) | | | |
|---|---|---|---|
| Evaluation point | E.3 | E.3.i | Result |
| 15 minutes | 4.3 | 3.8 | E.3 = E.3.i |
| 2 hours | 2.5 | 3.1 | E.3 = E.3.i |
| 3 hours | 2.6 | 3.4 | E.3 << E.3.i |

TABLE 29

| (Helvetolide ®[1]) + Linalyl Acetate) vs (Helvetolide ® + Linalyl Acetate + Haloscent ® D) | | | |
|---|---|---|---|
| Evaluation point | E.6 | E.6.i | Result |
| 15 minutes | 3.3 | 4.5 | E.6 << E.6.i |
| 45 minutes | 2.8 | 3.5 | E.6 << E.6.i |
| 2 hours | 1.8 | 2.7 | E.6 << E.6.i |
| 3 hours | 2.7 | 3.0 | E.6 = E.6.i |

TABLE 30

| (Helvetolide ® + Citronellol) vs (Helvetolide ® + Citronellol + Haloscent ® D) | | | |
|---|---|---|---|
| Evaluation point | E.7 | E.7.i | Result |
| 15 minutes | 5.3 | 5.2 | E.7 = E.7.i |
| 45 minutes | 2.3 | 4.3 | E.7 << E.7.i |
| 2 hours | 2.2 | 3.3 | E.7 << E.7.i |
| 3 hours | 1.4 | 1.8 | E.7 = E.7.i |

TABLE 31

| (Exaltolide ®[2]) + Linalyl Acetate) vs (Exaltolide ® + Linalyl Acetate + Haloscent ® D) | | | |
|---|---|---|---|
| Evaluation point | E.8 | E.8.i | Result |
| 15 minutes | 4.0 | 4.4 | E.8 = E.8.i |
| 45 minutes | 2.2 | 2.9 | E.8 << E.8.i |
| 2 hours | 2.6 | 3.2 | E.8 << E.8.i |
| 3 hours | 2.1 | 3.1 | E.8 << E.8.i |

1) pentadecanolide; origin: Firmenich SA

TABLE 32

| (Geraniol + Linalyl Acetate) vs (Geranionl + Linalyl Acetate + Haloscent ® D) | | | |
|---|---|---|---|
| Evaluation point | E.9 | E.9.i | Result |
| 15 minutes | 4.4 | 4.5 | E.9 = E.9.i |
| 2 hours | 2.9 | 4.3 | E.9 << E.9.i |
| 3 hours | 2.6 | 3.6 | E.9 << E.9.i |

TABLE 33

| (Hedione ®[1]) + Linalyl Acetate) vs (Hedione ® + Linalyl Acetate + Haloscent ® D) | | | |
|---|---|---|---|
| Evaluation point | E.10 | E.10.i | Result |
| 15 minutes | 3.3 | 4.4 | E.10 << E.10.i |
| 30 minutes | 3.4 | 4.2 | E.10 << E.10.i |
| 45 minutes | 2.0 | 3.2 | E.10 << E.10.i |

[1] see Example 2

TABLE 34

| (Hedione ® + Citronellol) vs E = (Hedione ® + Citronellol + Haloscent ® D) | | | |
|---|---|---|---|
| Evaluation point | E.11 | E.11.i | Result |
| 15 minutes | 5.4 | 5.5 | E.11 = E.11.i |
| 45 minutes | 3.3 | 2.8 | E.11 > E.11.i |
| 2 hours | 2.2 | 2.9 | E.11 < E.11.i |
| 3 hours | 2.2 | 3.2 | E.11 << E.11.i |

TABLE 35

| (Salicylate de Benzyle + Linalyl Acetate) vs (Benzyl salicylate + Linalyl Acetate + Haloscent ® D) | | | |
|---|---|---|---|
| Evaluation point | E.12 | E.12.i | Result |
| 15 minutes | 4.2 | 3.6 | E.12 = E.12.i |
| 2 hours | 2.6 | 2.3 | E.12 = E.12.i |
| 3 hours | 2.6 | 3.2 | E.12 << E.12.i |

TABLE 36

| (Citronellol + Romandolilde ®) vs (Citronellol + Romandolilde ® + Haloscent ® I) | | | |
|---|---|---|---|
| Evaluation point | G.1. | G.1.i | Result |
| 15 minutes | 5.0 | 4.7 | G.1 = G.1.i |
| 2 hours | 3.5 | 4.1 | G.1 = G.1.i |
| 3 hours | 2.9 | 3.6 | G.1 << G.1.i |

TABLE 37

(Methylcitral + Helvetolide ®) vs Methylcitral + Helvetolide ® + Haloscent ® I)

| Evaluation point | G.2 | G.2.i | Result |
|---|---|---|---|
| 15 minutes | 5.0 | 5.3 | G.2 = G.2.i |
| 2 hours | 4.2 | 4.3 | G.2 = G.2.i |
| 3 hours | 2.7 | 3.9 | G.2 << G.2.i |

TABLE 38

(Citral) vs (Citral + Haloscent ® D + Haloscent ® I)

| Evaluation point | I.1 | I.1.i | Result |
|---|---|---|---|
| 15 minutes | 3.7 | 4.3 | I.1 << I.1.i |
| 2 hours | 2.7 | 3.4 | I.1 << I.1.i |
| 3 hours | 1.7 | 2.5 | I.1 << I.1.i |

TABLE 39

(Citronellol) vs (Citronellol + Haloscent ® D + Haloscent ® I)

| Evaluation point | I.2 | I.2.i | Result |
|---|---|---|---|
| 15 minutes | 4.5 | 5.2 | I.2 << I.2.i |
| 2 hours | 3.1 | 4.0 | I.2 << I.2.i |
| 3 hours | 2.5 | 4.0 | I.2 << I.2.i |

TABLE 40

(Astrotone) vs (Astrotone + Haloscent ® D + Haloscent ® I)

| Evaluation point | I.3 | I.3.i | Result |
|---|---|---|---|
| 15 minutes | 3.5 | 4.7 | I.3 << I.3.i |
| 2 hours | 3.0 | 4.3 | I.3 << I.3.i |
| 3 hours | 2.8 | 3.7 | I.3 << I.3.i |

TABLE 41

(Exaltolide ®) vs (Exaltolide ® + Haloscent ® D + Haloscent ® I)

| Evaluation point | I.4 | I.4.i | Result |
|---|---|---|---|
| 15 minutes | 3.1 | 4.1 | I.4 << I.4.i |
| 2 hours | 2.8 | 4.2 | I.4 << I.4.i |
| 3 hours | 2.5 | 3.6 | I.4 << I.4.i |

TABLE 42

(Romandolide ® ) vs (Romandolide ® + Haloscent ® D + Haloscent ® I)

| Evaluation point | I.5 | I.5.i | Result |
|---|---|---|---|
| 15 minutes | 3.2 | 4.5 | I.5 << I.5.i |
| 2 hours | 3.2 | 4.5 | I.5 << I.5.i |
| 3 hours | 2.2 | 3.4 | I.5 << I.5.i |

TABLE 43

(Helvetolide ®) vs Helvetolide ® + Haloscent ® D + Haloscent ® I)

| Evaluation point | I.6 | I.6.i | Result |
|---|---|---|---|
| 15 minutes | 3.1 | 4.3 | I.6 << I.6.i |
| 2 hours | 3.4 | 4.1 | I.6 << I.6.i |
| 3 hours | 2.8 | 3.8 | I.6 << I.6.i |

TABLE 44

(Hedione ®) vs (Hedione ® + Haloscent ® D + Haloscent ® I)

| Evaluation point | I.7 | I.7.i | Result |
|---|---|---|---|
| 15 minutes | 2.3 | 3.6 | I.7 << I.7.i |
| 2 hours | 2.3 | 4.0 | I.7 << I.7.i |
| 3 hours | 1.8 | 3.0 | I.7 << I.7.i |

TABLE 45

(tetrahydro-2-isobutyl-4-methyl-4(2H)-pyranol) vs (tetrahydro-2-isobutyl-4-methyl-4(2H)-pyranol + Haloscent ® D + Haloscent ® I)

| Evaluation point | I.9 | I.9.i | Result |
|---|---|---|---|
| 15 minutes | 2.9 | 3.9 | I.9 << I.9.i |
| 2 hours | 2.6 | 2.6 | I.9 = I.9.i |
| 3 hours | 2.7 | 2.0 | I.9 = I.9.i |

It can be seen that each time the invention's composition of matter perform better that the single acyclic perfuming mono-terpenes derivative with either a musk, or another acyclilc perfuming mono-terpenes derivatives or an optional ingredient. When instead of the component a) is used a similar compound (i.e. the corresponding perfumery raw material) the effect is not observed anymore.

EXAMPLE 2

Preparation of Perfuming Composition According to the Invention a) A compounded perfume A.1) for preparing an eau de toilette was prepared by admixing the following ingredients:

| Ingredient | % w/w |
|---|---|
| Linalyl acetate | 20.83 |
| Bergamot oil[1] | 8.33 |
| Lemon oil[2] | 4.17 |
| Corolle[3] | 3.33 |
| Dipropyleneglycol | 29.67 |
| 1% BHT[4] | 1.00 |
| Hedione ®[5] | 20.83 |
| Lavender oil[6] | 4.34 |
| Crystal Moss | 0.42 |
| Muscenone ®[7] Delta | 0.75 |
| Muscenone ®[7] Dextro | 0.08 |

-continued

| Ingredient | % w/w |
|---|---|
| Patchouli oil | 1.67 |
| Romandolide ®[8)] | 4.17 |
| Clary sauge oil[9)] | 0.42 |
| | 100.00 |

[1)]Contains 62 w/w % of compounds b)
[2)]Contains 6.6 w/w % of compounds b)
[3)]Compounded perfumery bases, contains 60 w/w % of compounds b); origin: Firmenich
[4)]2,6-di-tert-butyl-4methylphenol 1% in Dipropyleneglycol
[5)]Methyl dihydrojasmonate; origin: Firmenich SA, Geneva, Switzerland
[6)]Contains 66 w/w % of compounds b)
[7)]3-Methyl-5-cyclopentadecen-1-one; origin: Firmenich SA, Geneva, Switzerland
[8)](1S,1'R)-[1-(3',3'-Dimethyl-1'-cyclohexyl)ethoxycarbonyl]methyl propanoate; origin: Firmenich SA, Geneva, Switzerland
[9)]Contains 3.4 w/w % of compounds b)

A second compounded perfume A.2) was obtained by admixing the same ingredient but replacing 2.25% of DIPG line with 2.25% of 3-(dodecylthio)-1-(2,6,6-trimethylcyclohex-3-en-1-yl)butan-1-one.

Said perfume A.2) was thus characterized by an a)/b) ratio of 1/16 and an optional component)/b) ratio of 1/1.7.

Each of said A.1), A.2), was then diluted (eau de cologne) at 10% w/w into a mixture ethanol/water (79.6% w/w Ethanol and 10.42% w/w Demineralized water), to provide respectively the eau de cologne A.c.1) and A.c.2). 20 µl of said eau de cologne were then assessed according to the same panel protocol as described in Examples 1, and the results are reported in the following table.

TABLE 1

| odor intensity of the composition after a given time from application: | | | |
|---|---|---|---|
| Evaluation point | A.c.1) | A.c.2) | Result |
| 15 minutes | 4.6 | 5.3 | A.c.1) < A.c.2) |
| 2 hours | 3.5 | 3.8 | A.c.1) = A.c.2) |
| 3 hours | 2.4 | 3.0 | A.c.1) << A.c.2) |
| 5 hours | 3.2 | 3.2 | A.c.1) = A.c.2) |

As can be seen, the invention perfuming composition showed a significant improvement at least between 15 min to 3 hours from application.

The same Eau de toilette samples of Eau Fraîche A.1) and A.2) were assessed through a Quantitative Descriptive Analysis methodology (QDA). QDA is used to describe and quantify fragrance characteristics and provides a descriptive evaluation using a consensual vocabulary and a linear line scale. 8 to 12 Panelists are screened and trained for complex sensory tasks. This methodology is based on iterative process to generate language terms, where attributes are derived entirely from the panelists. Attributes are then defined, and reference materials are utilized in the evaluations. Three complete replications per panelist per sample are done. QDA utilizes a 10 cm semi-structured line intensity scale which is converted to numerical values from 0-10.

TABLE 1a

| Descriptive attributes | QDA odor intensity of each attribute after a given time from application: | | | | | |
|---|---|---|---|---|---|---|
| | 2 h | | 4 h | | 6 h | |
| | A.1) | A.2) | A.1) | A.2) | A.1) | A.2) |
| Bergamot | 3.60 | 2.90 | 2.70 | 3.70 | 3.10 | 3.40 |
| Lemon | 2.00 | 0.90 | 0.80 | 2.10 | 1.40 | 2.20 |
| Lychee | 2.40 | 2.30 | 1.80 | 2.60 | 2.30 | 2.60 |
| Peony | 2.80 | 1.60 | 1.40 | 2.50 | 2.40 | 2.80 |

There is a significative difference when the delta in means of scores is ≥0.8. Lemon note is perceived significantly more intense with Haloscent® D after 2 hours evaporation. In the mid times (4 h), citrucy notes (Lemon & Bergamot), fruity notes (Lychee) and floral notes (Peony) were also more intense in Eau Fraîche with Haloscent® D compared to Eau Fraîche without Haloscent® D.

b) A compounded perfume B.1) for preparing an eau de toilette was prepared by admixing the following ingredients:

| Ingredient | % w/w |
|---|---|
| Linalyl Acetate | 19.23 |
| Aldehyde C11 Lenique | 0.38 |
| Bergamot oil[1)] | 3.85 |
| Corolle[2)] | 7.69 |
| Dipropyleneglycol | 18.23 |
| 1% BHT[3)] | 1.00 |
| Gardenia oil | 0.38 |
| Habanolide ®[4)] | 3.85 |
| Hedione ®[5)] | 30.00 |
| Hedione ®[6)] HC | 3.85 |
| Iso E ®[7)] Super | 3.77 |
| Jasmin oil | 1.92 |
| Muscenone ®[8)] Delta | 0.38 |
| Muscenone ®[8)] Dextro | 0.08 |
| Neroli oil[9)] | 1.54 |
| Rose oil | 3.85 |
| | 100.00 |

[1)]Contains 62 w/w % of compounds b)
[2)]Compounded perfumery bases, contains 60 w/w % of compounds b); origin: Firmenich
[3)]2,6-di-tert-butyl-4methylphenol 1% in Dipropyleneglycol
[4)]pentadecenolide; origin:: Firmenich SA, Geneva, Switzerland
[5)]Methyl dihydrojasmonate; origin: Firmenich SA, Geneva, Switzerland
[6)]Methyl dihydrojasmonate high cis; origin: Firmenich SA, Geneva, Switzerland
[7)]1-(octahydro-2,3,8,8-tetramethyl-2-naphtalenyl)-1-ethanone; origin: International Flavors & Fragrances, USA
[8)]3-Methyl-5-cyclopentadecen-1-one; origin: Firmenich SA, Geneva, Switzerland
[9)]Contains 40 w/w % of compounds b)

A second compounded perfume B.2) was obtained by admixing the same ingredient but replacing 2.25% of DIPG line with 2.25% of 3-(dodecylthio)-1-(2,6,6-trimethylcyclohex-3-en-1-yl)butan-1-one.

Said perfume B.2) was thus characterized by an a)/b) ratio of 1/13.8 and an optional component)/b) ratio of 1.2/1.

A third compounded perfume B.3) was obtained by admixing the same ingredients but replacing 0.225% of DIPG line with 0.225% of 3-(dodecylthio)-1-(2,6,6-trimethylcyclohex-3-en-1-yl)butan-1-one.

A fourth compounded perfume B.4) was obtained by admixing the same ingredients but replacing 0.225% of DIPG line with 0.225% of 4-(dodecylthio)-4-(2,6,6-trimethylcyclohex-2-en-1-yl)butan-2-one (Haloscent® I)

Each of said B.1), B.2), B.3), B.4) was then diluted (eau de cologne) at 10% w/w into a mixture ethanol/water (79.6% w/w Ethanol and 10.42% w/w Demineralized water), to provide respectively the eau de cologne B.c.1), B.c.2), B.c.3) and B.c.4). 20 μl of said eau de cologne were then assessed according to the same panel protocol as described in Examples 1, and the results are reported in the following tables:

TABLE 2 odor intensity of the composition after a given time from application:

| Evaluation point | B.c.1) | B.c.2) | Result |
| --- | --- | --- | --- |
| 15 minutes | 5.1 | 4.8 | B.c.1) = B.c.2) |
| 2 hours | 3.2 | 3.7 | B.c.1) = B.c.2) |
| 3 hours | 3.1 | 3.7 | B.c.1) < B.c.2) |
| 5 hours | 2.6 | 3.5 | B.c.1) << B.c.2) |

As can be seen, the invention perfuming composition showed a significant improvement at least between 3 to 5 hours from application.

TABLE 3 odor intensity of the composition after a given time from application:

| Evaluation point | B.c.1) | B.c.3) | Result |
| --- | --- | --- | --- |
| 15 minutes | 5.1 | 4.9 | B.c.1) = B.c.3) |
| 2 hours | 4.1 | 4.1 | B.c.1) = B.c.3) |
| 4 hours | 3.0 | 3.2 | B.c.1) = B.c.3) |
| 8 hours | 2.6 | 3.2 | B.c.1) < B.c.3) |

As can be seen, the invention perfuming composition showed a directional improvement from 4 to 8 hours from application.

TABLE 4 odor intensity of the composition after a given time from application

| Evaluation point | B.c.1) | B.c.4) | Result |
| --- | --- | --- | --- |
| 15 minutes | 5.0 | 5.2 | B.c.1) = B.c.4) |
| 2 hours | 3.7 | 4.1 | B.c.1) = B.c.4) |
| 4 hours | 3.4 | 4.3 | B.c.1) << B.c.4) |
| 8 hours | 2.9 | 3.9 | B.c.1) << B.c.4) |

As can be seen, the invention perfuming composition showed a significant improvement between 4 to 8 hours from application c) A compounded perfume C.1) for preparing an eau de toilette was prepared by admixing the following ingredients:

| Ingredient | % w/w |
| --- | --- |
| Linalyl Acetate | 25.00 |
| Bergamot oil[1] | 10.00 |
| Lemon oil[2] | 5.00 |
| Corolle[3] | 4.00 |
| Dipropyleneglycol | 24.00 |
| 1% BHT[4] | 1.00 |
| Hedione ®[5] | 25.00 |
| Muscenone ®[6] Delta | 0.90 |
| Muscenone ®[6] Dextro | 0.10 |
| Romandolide ®[7] | 5.00 |
| | 100.00 |

[1] Contains 62 w/w % of compounds b)
[2] Contains 6.6 w/w % of compounds b)
[3] Compounded perfumery bases, contains 60 w/w % of compounds b); origin: Firmenich
[4] 2,6-di-tert-butyl-4methylphenol 1% in Dipropyleneglycol
[5] Methyl dihydrojasmonate; origin: Firmenich SA, Geneva, Switzerland
[6] 3-Methyl-5-cyclopentadecen-1-one; origin: Firmenich SA, Geneva, Switzerland
[7] (1S,1'R)-[1-(3',3'-Dimethyl-1'-cyclohexyl)ethoxycarbonyl]methyl propanoate; origin: Firmenich SA, Geneva, Switzerland A second compounded perfume C.2) was obtained by admixing the same ingredient but replacing 2.25% of DIPG line with 2.25% of 3-(dodecylthio)-1-(2,6,6-trimethylcyclohex-3-en-1-yl)butan-1-one.

Said perfume C.2) was thus characterized by an a)/b) ratio of 1/17.7 and an optional component)/b) ratio of 1/1.6.

A third compounded perfume C.3) was obtained by admixing the same ingredient but replacing 0.83% of DIPG line with 0.83% of delta damascone.

A fourth compounded perfume C.4) was obtained by admixing the same ingredient but replacing 2.25% of DIPG line with 2.25% of 4-(dodecylthio)-4-(2,6,6-trimethylcyclohex-2-en-1-yl)butan-2-one (Haloscent® I)

Each of said C.1), C.2), C.3), C.4) was then diluted (eau de cologne) at 10% w/w into a mixture ethanol/water (79.6% w/w Ethanol and 10.42% w/w Demineralized water), to provide respectively the eau de cologne C.c.1), C.c.2) C.c.3) and C.c.4). 20 μl of said eau de cologne were the assessed according to the same panel protocol as described in Examples 1, and the results are reported in the following table.

TABLE 5 odor intensity of the composition after a given time from application:

| Evaluation point | C.c.1) | C.c.2) | C.c.3) | Result |
| --- | --- | --- | --- | --- |
| 15 minutes | 5.1 | 5.3 | 4.9 | C.c.1) = C.c.3) = C.c.2) |
| 2 hours | 2.6 | 3.4 | 2.9 | C.c.1) = C.c.3) << C.c.2) |
| 4 hours | 2.5 | 3.0 | 2.5 | C.c.1) = C.c.3) << C.c.2) |
| 8 hours | 2.3 | 3.2 | 1.8 | C.c.1) = C.c.3) << C.c.2) |

As can be seen, the invention perfuming composition showed a significant improvement at least between 2 to 8 hours from application. When instead of the component a) is used a similar compound (i.e. the corresponding perfumery raw material) the effect is not observed anymore.

TABLE 6 odor intensity of the composition after a given time from application:

| Evaluation point | C.c.1) | C.c.4) | Result |
| --- | --- | --- | --- |
| 15 minutes | 4.3 | 4.4 | C.c.1) = C.c.4) |
| 2 hours | 2.7 | 3.7 | C.c.1 << C.c.4) |
| 4 hours | 3.1 | 3.5 | C.c.1) = C.c.4) |

As can be seen, the invention perfuming composition showed a significant improvement at least at 2 hours from application.

The same Eau de toilette samples of BQ Cologne C.1) and C.2) were assessed through a Quantitative Descriptive Analysis methodology (QDA) as described in example a) above.

TABLE 5a odor intensity of each attribute after a given time from application:

| Descriptive attributes | 15 min | | 2 h | | 4 h | | 8 h | |
|---|---|---|---|---|---|---|---|---|
| | C.1) | C.2) | C.1) | C.2) | C.1) | C.2) | C.1) | C.2) |
| citrus | 3.6 | 3.4 | 2.3 | 3.1 | 2.4 | 2.8 | 1.7 | 2.0 |
| woody | 2.4 | 2.9 | 2.4 | 3.2 | 2.5 | 2.8 | 1.9 | 3.0 |
| musk | 3.1 | 3.7 | 2.6 | 2.9 | 3.1 | 3.3 | 2.3 | 3.2 |

After 15 mins from application, C.2 in the Eau de toilette had a directional improvement on intensity over C.1 on the musk attribute. After 2 hours, C.2 showed a significant improvement over C.1 on the intensity of the citrus attribute. After 8 hours, C.2 showed a significant improvement over C.1 on both the woody and musk attributes.

It is evident from above that the addition of Haloscent® D to the control not only impacts a significant improvement in overall intensity of the mixture but that it is capable of modulating top (citrus) and bottom notes (woody, musk) of the fragrance.

d) A compounded perfume D.1) for preparing an eau de toilette was prepared by admixing the following ingredients:

| Ingredient | % w/w |
|---|---|
| Benzyle Acetate | 0.32 |
| Linalyl Acetate | 21.56 |
| Aldehyde C 10 | 0.11 |
| Aldehyde C 8 | 0.11 |
| Levo Carvone | 0.11 |
| Citral | 3.23 |
| Lemon Oil[1] | 25.00 |
| Citronellol | 0.11 |
| Dipropyleneglycol | 0.90 |
| Pear Oil | 0.54 |
| 1% BHT[2] | 1.00 |
| Galbanolene | 0.11 |
| Iso E ®[3] Super | 5.39 |
| Lavander Oil[4] | 0.65 |
| Limonene[5] | 21.35 |
| Linalol | 7.76 |
| Methyle Methylanthranilate | 0.32 |
| Petitgrain | 4.31 |
| Romandolide ®[6] | 5.39 |
| 3-methyl-5-(2,2,3-trimethyl-3-cyclopenten-1-yl)-2-pentanol | 1.62 |
| Tarragol | 0.11 |
| | 100.00 |

[1]Contains 6.6 w/w % of compounds b)
[2]2,6-di-tert-butyl-4methylphenol 1% in Dipropyleneglycol
[3]1-(octahydro-2,3,8,8-tetramethyl-2-naphtalenyl)-1-ethanone; origin: International Flavors & Fragrances, USA
[4]Contains 66 w/w % of compounds b)
[5]Contains 0.30 w/w % of compounds b)
[6](1S,1'R)-[1-(3',3'-Dimethyl-1'-cyclohexyl)ethoxycarbonyl]methyl propanoate; origin: Firmenich SA, Geneva, Switzerland A second compounded perfume D.2) was obtained by admixing the same ingredient but replacing 2.25% of DIPG line with 2.25% of 3-(dodecylthio)-1-(2,6,6-trimethylcyclohex-3-en-1-yl)butan-1-one.

Said perfume D.2) was thus characterized by an a)/b) ratio of 1/18 and an optional component)/b) ratio of 1/7.5.

A third compounded perfume D.3) was obtained by admixing the same ingredient but replacing 0.83% of DIPG line with 0.83% of delta damascone.

A fourth compounded perfume D.4) was obtained by admixing the same ingredients but replacing 2.25% of DIPG with 2.25% of delta damascone.

Each of said D.1), D.2), D.3), D.4) was then diluted (eau de cologne) at 10% w/w into a mixture ethanol/water (79.6% w/w Ethanol and 10.42% w/w Demineralized water), to provide respectively the eau de cologne D.d.1), D.d.2), D.d.3) and D.d.4.). 20 μl of said eau de cologne were then assessed according to the same panel protocol as described in Examples 1, and the results are reported in the following table.

TABLE 7 odor intensity of the composition after a given time from application:

| Evaluation point | D.d.1) | D.d.2) | D.d.3) | D.d.4) | Result |
|---|---|---|---|---|---|
| 15 minutes | 4.1 | 4.6 | 4.0 | 4.1 | D.d.1) = D.d.3) = D.d.4) << D.d.2) |
| 1 hour | 3.4 | 3.8 | 3.3 | 3.3 | D.d.1) = D.d.3) = D.d.4) << D.d.2) |
| 4 hours | 1.5 | 1.9 | 1.5 | 0.9 | D.d.1) = D.d.3) = D.d.4) < D.d.2) |

As can be seen, the invention perfuming composition showed a significant improvement at least between 0 to 4 hours from application. When instead of the component a) is used a similar compound (i.e. the corresponding perfumery raw material) the effect is not observed anymore.

e) A compounded perfume E.1) for preparing an eau de toilette was prepared by admixing the following ingredients:

| Ingredient | % w/w |
|---|---|
| Rose oil | 2.94 |
| Orchid oil | 4.71 |
| Gardenia oil | 0.29 |
| Chantilly[4] | 4.11 |
| Corolle ®[3] | 5.88 |
| Linalyl Acetate | 17.65 |
| Aldehyde C11 | 0.003 |
| Bergamot oil | 2.94 |
| Maltol | 0.03 |
| DIPG | 16.06 |
| BHT | 0.07 |
| Habanolide ® | 2.94 |
| Iso E ®[2] Super | 8.77 |
| Jasmin oil | 1.47 |
| Muscenone ® Delta | 0.29 |
| Muscenone ® Dextro | 0.059 |
| Hedione ® | 23.53 |
| Neroli oil | 0.012 |
| Patchouli oil | 0.59 |
| Clearwood ®[1] | 0.59 |
| Benzyl Salicylate | 5.88 |
| Vainilline | 1.77 |
| | 100 |

[1]Terpenic fraction of Patchouli oil; origin: Firmenich SA, Geneva, Switzerland
[2]1-(octahydro-2,3,8,8-tetramethyl-2-naphtalenyl)-1-ethanone; origin: International Flavors & Fragrances, USA
[3]Compounded perfumery bases, contains 60 w/w % of compounds b); origin: Firmenich
[4]Compounded perfumery bases; origin: Firmenich A second compounded perfume E.2) was obtained by admixing the same ingredient but replacing 2.25% of DIPG line with 2.25% of 3-(dodecylthio)-1-(2,6,6-trimethylcyclohex-3-en-1-yl)butan-1-one. ratio a/b=1/11.7; ratio optional/b=1.45/1.

A third compounded perfume E.3) was obtained by admixing the same ingredient but replacing 2.25% of DIPG line with 2.25% of 4-(dodecylthio)-4-(2,6,6-trimethylcyclo-hex-2-en-1-yl)butan-2-one (Haloscent® I). ratio a/b=1/11.7; ratio optional/b=1.45/1.

A fourth compounded perfume E.4) was obtained by admixing the same ingredient but replacing 4.50% of DIPG line with 2.25% of 3-(dodecylthio)-1-(2,6,6-trimethylcyclo-hex-3-en-1-yl)butan-1-one and 2.25% of 4-(dodecylthio)-4-(2,6,6-trimethylcyclohex-2-en-1-yl)butan-2-one (Halo-scent® I).

Each of said E.1), E.2), E.3), E.4) was then diluted (eau de cologne) at 10% w/w into a mixture ethanol/water (79.6% w/w Ethanol and 10.42% w/w Demineralized water), to provide respectively the eau de cologne E.e.1), E.e.2), E.e.3) and E.e.4.). 20 µl of said eau de cologne were then assessed according to the same panel protocol as described in Examples 1, and the results are reported in the following tables:

TABLE 8 odor intensity of the composition after a given time from application:

| Evaluation point | E.e.1) | E.e.2) | Result |
|---|---|---|---|
| 15 minutes | 6.8 | 5.7 | E.e.1) = E.e.2) |
| 2 hours | 4.8 | 5.1 | E.e.1) = E.e.2) |
| 4 hours | 4.7 | 4.8 | E.e.1) = E.e.2) |
| 8 hours | 3.4 | 4.2 | E.e.1) << E.e.2) |

As can be seen, the invention perfuming composition showed a significant improvement at least at 8 hours from application

TABLE 9 odor intensity of the composition after a given time from application:

| Evaluation point | E.e.1) | E.e.3) | Result |
|---|---|---|---|
| 15 minutes | 4.5 | 5.5 | E.e.1) << E.e.3) |
| 2 hours | 4.0 | 4.9 | E.e.1) << E.e.3) |
| 4 hours | 4.2 | 3.7 | E.e.1) = E.e.3) |
| 8 hours | 4.0 | 3.7 | E.e.1) = E.e.3) |

As can be seen, the invention perfuming composition showed a significant improvement at least between 15 minutes and 2 hours from application.

TABLE 10 odor intensity of the composition after a given time from application

| Evaluation point | E.e.1) | E.e.4) | Result |
|---|---|---|---|
| 15 minutes | 4.7 | 4.5 | E.e.1) = E.e.4) |
| 2 hours | 4.1 | 4.8 | E.e.1) = E.e.4) |
| 4 hours | 3.9 | 4.2 | E.e.1) << E.e.4) |
| 8 hours | 3.5 | 4.0 | E.e.1) = E.e.4) |

As can be seen, the invention perfuming composition showed a significant improvement at least 4 hours from application.

The same Eau de toilette samples of E.1) and E.2) were assessed through a Quantitative Descriptive Analysis methodology (QDA) as described in example a) above.

TABLE 11 odor intensity of each attribute after a given time from application:

| Descriptive attributes | 15 min | | 2 h | | 4 h | | 8 h | |
|---|---|---|---|---|---|---|---|---|
| | E.1) | E.2) | E.1) | E.2) | E.1) | E.2) | E.1) | E.2) |
| Floral | 5.0 | 5.3 | 3.4 | 4.4 | 4.2 | 4.1 | 3.0 | 3.6 |
| Musk | 4.2 | 4.2 | 4.1 | 4.0 | 3.5 | 3.2 | 2.8 | 3.5 |

After 2 hours, E.2 showed a significant improvement over E.1 on the intensity of the floral attribute. After 8 hours, E.2 showed a significant improvement over E.1 on the floral attribute, and a directional improvement on the intensity of the musk attribute. It is evident from above that the addition of Haloscent® D to the control not only impacts a significant improvement in overall intensity of the mixture but that it is capable of lit modulating notes (floral, musk) of the fragrance.

The invention claimed is:
1. A perfuming composition comprising:
 a) at least one β-thio carbonyl profragrance derivative of formula

(I)

wherein the wavy line indicates the location of the bond between said P and the sulfur atom;
 P represents a group of the formulae (P-1) to (P-9), in the form of any one of their isomers:

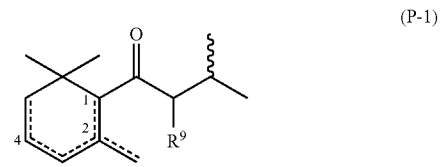
(P-1)

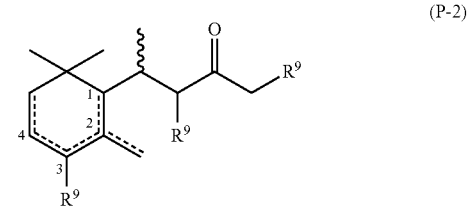
(P-2)

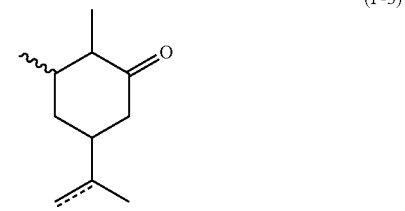
(P-3)

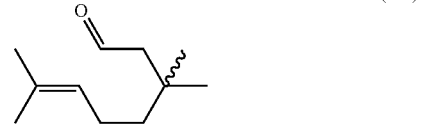
(P-4)

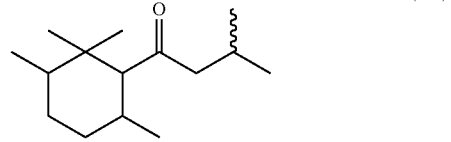
(P-5)

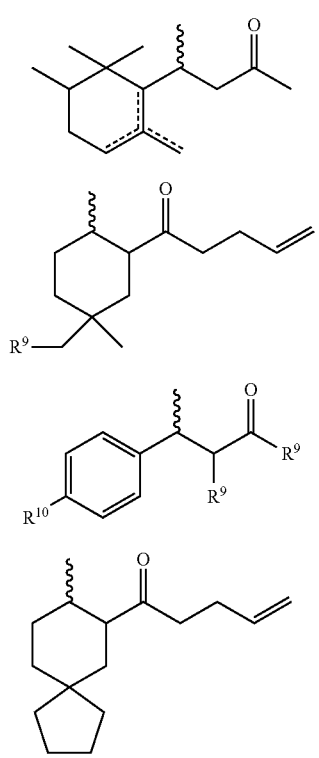

in which formulae the wavy lines have the meaning indicated above and the dotted lines represent a single or double bond, and $R^9$ being a hydrogen atom or a methyl group; and R represents a linear or branched alkyl group having from 8 to 15 carbon atoms, optionally comprising a carboxylic functional group which is not directly linked to the sulphur atom; and b) at least one perfume ingredient selected among:
acyclic mono-terpenes derivatives; and/or
musk compounds;
said components a) and b) being present in a w/w (weight to weight) ratio a)/b) comprised between 1/1 and 1/4500;
wherein fragrance intensities of top notes and bottom notes of the at least one perfume ingredient are enhanced by the presence of the at least one β-thio carbonyl profragrance derivative.

2. The perfuming composition according to claim 1, characterized in that said at least one perfume ingredient b) is selected amongst acyclic mono-terpenes derivatives.

3. The perfuming composition according to claim 1, wherein said at least one β-thio carbonyl profragrance derivative of formula (I) is a derivative wherein P is a group of the formulae (P-1), (P-2), (P-5) or (P-6).

4. The perfuming composition according to claim 1, wherein said at least one β-thio carbonyl profragrance derivative of formula (I) is 3-(dodecylthio)-1-(2,6,6-trimethylcyclohex-3-en-1-yl)butan-1-one or 3-(dodecylthio)-1-(2,6,6-trimethylcyclohex-2-en-1-yl)butan-1-one or 4-(dodecylthio)-4-(2,6,6-trimethylcyclohex-2-en-1-yl)butan-2-one, or a mixture thereof.

5. The perfuming composition according to claim 1, wherein said acyclic perfuming mono-terpenes derivatives is:

geraniol, nerol, citronellol, dihydrolinalool, linalool, ethyl linalool, myrcenol, dihydro myrcenol;
citral, 3-Me-citral, citronellal, geranial, hydroxycitronellal;
citronellyl acetate, linalyl acetate, geranyl acetate, linalyl propionate, neryl acetate, linalyl caproate, geranyl tiglate;
linalyl methyl ether;
citronellyl nitrile;
a stereoisomer of any of the foregoing compounds; or
a mixture of any of the foregoing compounds.

6. The perfuming composition according to claim 5, characterized in that said acyclic perfuming mono-terpenes derivatives is:
citronellol, dihydrolinalool, linalool;
3-Me-citral, citronellal;
citronellyl acetate, linalyl acetate;
citronellyl nitrile;
a stereoisomer of any of the foregoing compounds; or
a mixture of any of the foregoing compounds.

7. The perfuming composition according to claim 1, wherein said musk compound is:
(1S,1'R)-2-[1-(3',3'-dimethyl-1'-cyclohexyl)ethoxycarbonyl]methyl propanoate, (1S,1'R)-2-[1-(3',3'-dimethyl-1'-cyclohexyl)ethoxy]-2-methylpropyl propanoate, 2-[1-(3,3-dimethylcyclohexyl)ethoxy]-2-methylpropyl cyclopropanecarboxylate, 2-[(3,5-dimethyl-3-hexen-2-yl)oxy]-2-methylpropyl cyclopropanecarboxylate, 1-[(1R)-3,3-dimethylcyclohexyl]ethyl propanedioate; or
1-oxa-12-cyclohexadecen-2-one, oxacyclohexadecan-2-one, 1,4-dioxacycloheptadecane-5,17-dione, 3-methyl-(4/5)-cyclopentadecenone, muscone, (Z)-4-cyclopentadecen-1-one, 9-cycloheptadecen-1-one and/or 1,3,4,6,7,8-hexahydro-4,6,6,7,8,8-hexamethyl-cyclopenta-[G]isochromene.

8. The perfuming composition according to claim 1, further comprising, one or more optional components of other perfuming ingredients of:
methyl 2-(3-oxo-2-pentylcyclopentyl)acetate, (+)-methyl (1R)-cis-3-oxo-2-pentyl-1-cyclopentaneacetate, benzyl salicylate, tetrahydro-2-isobutyl-4-methyl-4 (2H)-pyranol, 3-benzodioxole-5-propionaldehyde;
coumarine, and/or 1-(octahydro-2,3,8,8-tetrame-2-naphthalenyl)-1-ethanone;
a stereoisomer of any of the foregoing compounds; or
a mixture of any of the foregoing compounds.

9. The perfuming composition according to claim 8, wherein said optional components can be present in a w/w ratio of (optional components)/b) comprised between 0 and 4.

10. A perfuming composition comprising:
i) as perfuming ingredient, the perfuming composition of claim 1;
ii) at least one ingredient selected from the group consisting of a perfumery carrier and a perfumery base; and
iii) optionally at least one perfumery adjuvant.

11. A method to boost, enhance, modulate, improve or increase the odor properties of a perfuming composition or of a perfumed consumer product, which method comprises adding to said composition or consumer product an effective amount of the perfuming composition of claim 1.

12. A perfuming consumer product having a total amount of surfactant below 20% w/w, the percentage being relative to the weight of the perfuming consumer product formulation, comprising, as a perfuming ingredient, the perfuming composition of claim 1.

13. The perfuming consumer product according to claim 12, characterized in that the total amount of surfactant is below 6% w/w.

14. The perfuming consumer product according to claim 12, wherein said perfuming consumer product is a perfume, a deodorant or antiperspirant or a cosmetic composition.

15. The perfuming consumer product according to claim 14, characterized in that said perfuming consumer product is a fine perfume, eau de toilette, eau de perfume, cologne, body splash, after shave lotion or body spray, or body mist.

16. The perfuming composition of claim 1 which is free of sulfites.

17. A method to improve fragrance intensities of top notes and bottom notes of a fragrance which comprises incorporating in a perfumed consumer product a fragrance effective amount of the perfuming composition of claim 1.

18. The method of claim 17, wherein the perfumed consumer product is a perfume, a deodorant or antiperspirant or a cosmetic composition.

19. The method of claim 18, wherein the perfumed consumer product is a fine perfume, eau de toilette, eau de perfume, cologne, body splash, after shave lotion or body spray, or body mist.

\* \* \* \* \*